United States Patent [19]

Adam-Molina

[11] Patent Number: 4,647,457
[45] Date of Patent: Mar. 3, 1987

[54] PENICILLANIC ACID DERIVATIVES

[75] Inventor: Solange Adam-Molina, Rosenau, France

[73] Assignee: Hoffmann-La Roche Inc., Nutley, N.J.

[21] Appl. No.: 585,741

[22] Filed: Mar. 2, 1984

[30] Foreign Application Priority Data

Dec. 16, 1983 [CH] Switzerland .................... 6710/83

[51] Int. Cl.$^4$ ................. C07D 499/00; A61K 31/425
[52] U.S. Cl. ...................................... 424/114; 514/194; 514/195; 514/196; 544/133; 540/310
[58] Field of Search ................ 260/245.2 R; 424/270, 424/114; 514/194, 196, 195; 544/133

[56] References Cited

U.S. PATENT DOCUMENTS

| | | | |
|---|---|---|---|
| 3,714,156 | 1/1973 | Rapoport | 260/243 C |
| 4,020,077 | 4/1977 | Cook et al. | 424/270 |
| 4,053,468 | 10/1977 | Holden | 544/16 |
| 4,087,424 | 5/1978 | Saikawa et al. | 544/26 |
| 4,123,539 | 10/1978 | DiNinno | 260/243 C |
| 4,143,046 | 3/1979 | Sheehan | 260/243 C |
| 4,207,323 | 6/1980 | Beattie et al. | 424/270 |
| 4,236,001 | 11/1980 | Gleason | 544/26 |
| 4,272,439 | 6/1981 | Ganguly et al. | 260/245.2 R |
| 4,282,149 | 8/1981 | Sheehan et al. | 260/245.2 R |

FOREIGN PATENT DOCUMENTS

| | | |
|---|---|---|
| 50805 | 5/1982 | European Pat. Off. |
| 2416492 | 10/1974 | Fed. Rep. of Germany |
| 2546243 | 5/1976 | Fed. Rep. of Germany |
| 2824535 | 12/1978 | Fed. Rep. of Germany |

OTHER PUBLICATIONS

J. Org. Chem. 38:3227 (1973).
J. Org. Chem. 40:191 (1975).
J. Org. Chem. 42:3972 (1977).
J. Org. Chem. 42:4045 (1977).
J. Chem. Soc. Perkin I, 2455 (1979).
Arisawa and Adam, Biochem. J. 211:447–454 (May 1983).

Primary Examiner—Nicholas S. Rizzo
Attorney, Agent, or Firm—Jon S. Saxe; Bernard S. Leon; George W. Johnston

[57] ABSTRACT

β-lactams of the formula

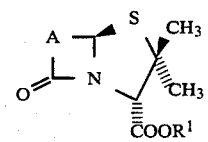

wherein $R^1$ signifies hydrogen or a group readily cleavable by hydrolysis, A signifies the group $R^2-N=C(CH_3)-CH=C<$ or $O=C(CH_3)-CH_2-C(R^3)<$, $R^2$ signifies hydroxy, lower alkoxy or arylamino and $R^3$ signifies arylthio, lower alkanoylthio, lower alkoxycarbonylhydrazino or a N-containing saturated heterocycle attached via a N-atom, and pharmaceutically acceptable salts thereof, are disclosed. The compounds and their salts exhibit β-lactamase inhibiting activities against β-lactamases from bacteria.

27 Claims, No Drawings

PENICILLANIC ACID DERIVATIVES

BACKGROUND OF THE INVENTION

This invention relates to beta-lactams.

SUMMARY OF THE INVENTION

The present invention is concerned with beta-lactams of the formula

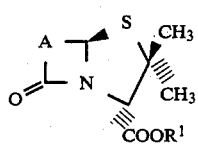

wherein $R^1$ signifies hydrogen or a group readily cleavable by hydrolysis, A signifies the group $R^2-N=C(CH_3)-CH=C<$ or $O=C(CH_3)-CH_2-C(R^3)<$, $R^2$ signifies hydroxy, lower alkoxy or arylamino and $R^3$ signifies arylthio, lower alkanoylthio, lower alkoxycarbonylhydrazino or a N-containing saturated heterocycle attached via a N-atom, and pharmaceutically acceptable salts of compounds of formula I in which $R^1$ signifies hydrogen with bases.

These compounds are novel and are distinguished by valuable therapeutic properties. In particular, they have pronounced β-lactamase-inhibiting properties and are therefore useful in the control of β-lactamase-forming pathogens in combination with β-lactamase-sensitive β-lactam antibiotics.

Objects of the present invention are β-lactams of general formula I above and pharmaceutically acceptable salts thereof with bases per se and as pharmaceutically active substances, the manufacture of these compounds, medicaments containing a compound of formula I or a pharmaceutically acceptable salt thereof with a base and the manufacture of such medicaments, as well as the use of compounds of formula I and of pharmaceutically acceptable salts thereof with bases in the control or prevention of illnesses.

DETAILED DESCRIPTION OF THE INVENTION

The present invention concerns beta-lactams of the formula

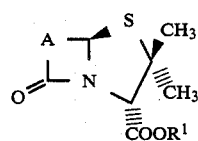

wherein $R^1$ is hydrogen or a group readily cleavable by hydrolysis: A is $R^2-N=C(CH_3)-CH=C<$ or $O=C(CH_3)-CH_2-C(R^3)<$; $R^2$ is hydroxy, lower alkoxy or arylamino; and $R^3$ is arythio, lower alkanoylthio; lower alkoxycarbonylhydrazino or a N-containing saturated heterocycle attached via its nitrogen atom, or a pharmaceutically acceptable salt thereof.

These compounds are novel and are distinguished by valuable therapeutic properties. In particular, they have pronounced β-lactamase-inhibiting properties and are therefore useful in the control of β-lactamase-forming pathogens in combination with β-lactamase-sensitive β-lactam antibiotics.

As used herein, the term "group readily cleavable by hydrolysis" signifies a conventional group cleavable under neutral, mild acidic or mild basic conditions or a conventional type cleavable enzymatically (i.e. by an esterase). Examples of such groups, which can be of the customary kind, are alkanoyloxyalkyl groups such as pivaloyloxymethyl, acetoxymethyl, 1-pivaloyloxyethyl and 1-acetoxyethyl; alkoxycarbonyloxyalkyl groups such as methoxycarbonyloxymethyl, 1-ethoxycarbonyloxyethyl and 1-isopropoxycarbonyloxyethyl; lactonyl groups such as phthalidyl and thiophthalidyl; alkoxymethyl groups such as methoxymethyl; and alkanoylaminomethyl groups such as acetamidomethyl.

The term "alkyl" denotes straight-chain or branched-chain saturated hydrocarbon groups of 1 to 12 carbon atoms (e.g., methyl, ethyl, n-propyl, isopropyl, n-butyl, s-butyl, t-butyl, octyl and the like).

The term "alkoxy" denotes alkyl groups attached via an oxygen atom (e.g., methoxy, ethoxy, n-propoxy, isopropoxy, octyloxy and the like.)

The term "lower alkyl" as well as other groups in the specification containing this term denotes groups and compounds containing alkyl radicals of at most 7, preferably at most 4, carbon atoms.

The term "hetero atom" denotes oxygen, nitrogen or sulphur.

The term "alkanoyl" denotes straight-chain or branched-chain fatty acid residues derived from alkanecarboxylic acid moieties (e.g., formyl, acetyl, propionyl, etc.).

The term "N-containing heterocycle" denotes a 5-membered or 6-membered saturated heterocycle ring containing a nitrogen atom which, in addition to the nitrogen atom, can contain a second hetero atom, for example an oxygen, sulphur or nitrogen atom, (e.g., morpholino).

The term "aryl" or any other group in the specification defined to include such term signifies a mononuclear or a dinuclear aromatic hydrocarbon group which is unsubstituted or substituted in one or more positions with lower alkylenedioxy, halogen, nitro, lower alkyl or lower alkoxy. Suitable aryl groups are unsubstituted or substituted phenyl and naphthyl. An aryl group may also contain one or more hetero atoms and therefore encompasses hetercycle rings (e.g., 2-benzothiazolyl.)

The term "halogen" signifies fluorine, chlorine, bromine and iodine.

The term "pharmaceutically acceptable salts thereof with bases" or "pharmaceutically acceptable salts" in this specification signifies, of course, pharmaceutically acceptable salts of carboxylic acids within formula I (i.e., $R^1$ is hydrogen) with conventional bases.

Among the compounds of formula I there are preferred those in which $R^1$ signifies hydrogen or pivaloyloxymethyl. $R^2$ preferably signifies hydroxy and $R^3$ preferably signifies phenylthio, acetylthio or morpholino.

Preferred compounds in the scope of the present invention are:

Methylene-(2S,5R)-6-[2-(hydroxyimino)-propylidene]penicillanate pivalate, methylene-(2S,5R,6S)-6-acetonyl-6-phenylthio-penicillanate pivalate, methylene-(2S,5R,6R)-6-acetonyl-6-acetylthio-penicillanate pivalate and methylene-(2S,5R,6S)-6-acetonyl-6-morpholino-penicillanate pivalate.

Further compounds in accordance with the invention are:

Methylene-(2S,5R)-6-[[2-(2-benzothiazolyl)hydrazono]propylidene]penicillanate pivalate,
methylene-(2S,5R)-6-[(E/Z)-2-(methoxyimino)-propylidene]penicillanate pivalate and
methylene-(2S,5R,6S)-acetonyl-6-[1-(ethoxyformamido)amino]penicillanate pivalate.

The compounds of formula I and their pharmaceutically acceptable salts with bases can be manufactured in accordance with the invention by reacting a compound of the formula

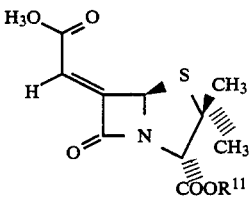

wherein $R^{11}$ signifies a group readily cleavable by hydrolysis, with a compound of the formula

  III or

  IV wherein $R^2$ and $R^3$ have the above significance, and, if desired, hydrolyzing a resulting compound of formula I in which $R^1$ signifies a group readily cleavable by hydrolysis and, also if desired, converting a resulting compound of formula I in which $R^1$ signifies hydrogen with a base into a pharmaceutically acceptable salt.

The reaction of a compound of formula II with a compound of formula III or IV can be carried out in a manner known per se. Suitable solvents for this reaction are, for example, lower alcohols such as ethanol, mixtures thereof with ethers such as tetrahydrofuran, and halogenated hydrocarbons such as methylene chloride. The reaction can be accelerated by the addition of a catalytic amount of a strong base such as, for example, DBN (1,5-diazabicyclo[4,3,0]non-5-ene). The reaction is conveniently carried out at a temperature between about 0° C. and about 50° C.

The hydrolysis of a compound of formula I in which $R^1$ signifies a group readily cleavable by hydrolysis can be carried out according to methods which are known per se and which are usual in such hydrolyses, whereby the choice of the suitable method and of the suitable reaction conditions presents no difficulties to a person skilled in the art. In a preferred embodiment, this hydrolysis is carried out enzymatically with an esterase such as, for example, pig liver esterase in an aqueous buffered system usual in such reactions, for example in phosphate buffer (pH 7), whereby, if desired, solubilizers such as dimethyl sulphoxide or the like can be added. As is usual in such cases, the hydrolysis is carried out in a temperature range of about 20° C. to 40° C.

The compounds of formula I in which $R^1$ signifies hydrogen can be converted with a conventional base into a pharmaceutically acceptable salt. Suitable bases are, for example, inorganic bases such as sodium hydroxide, potassium hydroxide, calcium hydroxide, sodium carbonate, potassium carbonate, calcium carbonate, sodium bicarbonate, potassium bicarbonate, calcium bicarbonate or the like and organic bases such as triethylamine, piperidine, diethylamine or the like. Such salts can be manufactured readily by any person skilled in the art having regard to the state of the art and the nature of the present compounds.

The compounds of formulae II, III and IV used as starting materials are either known or can be prepared from known compounds in a known manner which is analogous to preparing known members of these classes of substance.

As mentioned earlier, the compounds of formula I and pharmaceutically acceptable salts thereof with bases exhibit pronounced β-lactamase-inhibiting activities against β-lactamases from various strains of bacteria. As illustrated in the following experiments, these therapeutically valuable properties can be determined on isolated β-lactamases in vitro. In the experiments, ΔA is the difference of the absorption values measured.

A. Isolation of the β-lactamases

Various β-lactamases can be isolated from penicillin-resistant or cephalosphorin-resistant strains of bacteria such as Klebsiella pneumoniae NCTC 418, *Proteus vulgaris* 1028 and *E. coli* RTEM. For this purpose, the corresponding strains are cultivated in Tryptic Soy Broth (Difco) and harvested by centrifugation in the late logarithmic growth phase (when required 50–100 mg/l of ampicillin are added to the medium towards the end of the log-phase in order to induce the β-lactamase). The thus-obtained bacteria mass is treated with 10 mM of phosphate buffer (pH 7.0); the cells are broken open with ultrasound (Biosonic III, Bronwill; 3–5 min. impulse) while cooling. The mixture is centrifuged (20,000 r/min.) for 20–30 minutes and there is obtained a clear crude extract which can be used as the enzyme source (β-lactamase source) and which can be frozen at −20° C. for several months without loss of activity.

B. Determination of the β-lactamase activity

The determination of the activity of the isolated β-lactamases can be carried out according to the method of O'Callaghan, C. H. et al. [Antimicr. Ag. Chemother. 1, 283–288 (1972)] with the chromogenic cephalosporin nitrocefin (Glaxo). The required experimental batch contains per ml of water: 50 mM of phosphate buffer (pH 7.0), 0.1 mM of nitrocefin and sufficient enzyme (β-lactamase) in order to attain a ΔA/min. of about 0.1. The cleavage of the substrate, which is associated with a colour change, is carried out at 37° C. and is followed quantitatively at 482 nm with a spectral photometer.

C. Determination of the β-lactamase-inhibiting activity of the compounds of formula I The above-described cleavage of the chromogenic substrate by β-lactamases (experiment B) can be inhibited by adding compounds of formula I (inhibitors). Since it has been shown that the inhibitors irreversibly inactivate the β-lactamase in a time-dependent reaction, the reaction (cleavage of the substrate) is started by adding the substrate, in each case after a pre-incubation period of β-lactamase with inhibitor of 15 minutes. The determination of the β-lactamase-inhibiting activity of compounds of formula I in which $R^1$ signifies a group readily cleavable by hydrolysis is carried out in each case in the presence or absence of an esterase. As a measurement for the affinity of the respective tested inhibitor to the β-lactamase, which represents a measurement of the strength of the inhibitor, there serves that concentration which inhibits to 50% (IC 50 in μM/l) the cleavage of the substrate (nitrocefin) carried out under the above experimental conditions (experiment B) in the absence of an inhibitor. 4 to 6 experiments with differing concentrations of inhibitor were carried out in order to determine the IC 50. The determination of the IC 50 was carried out graphically.

The results obtained in the above experiment (experiment C) are given in the following Table:

varying the osmotic pressure, buffers, coating agents or antioxidants. They can also contain still other therapeutically valuable substances.

In general, compound I (or pharmaceutically acceptable salts thereof) amounts to about 0.05% to about 90% by weight of the inventive preparation.

The carboxylic acids of formula I and their pharmaceutically acceptable salts with bases are preferably administered parenterally and for this purpose are preferably prepared as lyophilizates or dry powders. The

TABLE

| Compound of Formula I | | β-Lactamase inhibition IC$_{50}$ in μM/l | | | | | |
|---|---|---|---|---|---|---|---|
| | | P. vulgaris 1028 | | K. pneumoniae NCTC 418 | | E. coli RTEM | |
| R$^1$ | A | −E | +E | −E | +E | −E | +E |
| (CH$_3$)$_3$CCOOCH$_2$— | HON=C(CH$_3$)—CH=C⟨ | 0.46 | 0.035 | 0.71 | 0.05 | 0.06 | 0.002 |
| (CH$_3$)$_3$CCOOCH$_2$— | O=C(CH$_3$)—CH$_2$—C(Sφ)⟨ | 3.7 | 0.3 | 44 | 0.1 | 0.8 | 0.002 |
| (CH$_3$)$_3$CCOOCH$_2$— | O=C(CH$_3$)—CH$_2$—C(SAc)⟨ | 4.2 | 0.2 | 4.6 | 0.1 | 0.7 | 0.01 |
| (CH$_3$)$_3$CCOOCH$_2$— | O=C(CH$_3$)—CH$_2$—C(Mo)⟨ | 4.1 | 0.1 | 6.3 | 0.1 | 0.9 | 0.01 |

−E = in the absence of an esterase
+E = in the presence of an esterase
φ = Phenyl;
Ac = acetyl;
Mo = morpholino The compounds of formula I and pharmaceutically acceptable salts thereof with bases can be used, for example, in the form of pharmaceutical preparations. The pharmaceutical preparations can be administered orally, for example in the form of tablets, coated tablets, dragées, hard and soft gelatine capsules, solutions, emulsions or suspensions. The administration can, however, also be carried out rectally (e.g. in the form of suppositories) or parenterally (e.g. in the form of injection solutions).

For the manufacture of tablets, coated tablets, dragées and hard gelatine capsules, the compounds of formula I and pharmaceutically acceptable salts thereof with bases can be processed with pharmaceutically inert, inorganic or organic carriers. Examples of such carriers which can be used for tablets, dragées and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols etc. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils etc. Suitable carriers for suppositories are, for example, natural or hardened oils, waxes, fats, semi-liquid or liquid polyols and the like.

Moreover, the pharmaceutical preparations can contain preserving agents, solubilizing agents, stabilizing agents, wetting agents, emulsifying agents, sweetening agents, colouring agents, flavouring agents, salts for readily hydrolyzable esters of formula I are preferably administered enterally.

As mentioned earlier, compounds of formula I and pharmaceutically acceptable salts thereof with bases can be used in accordance with the invention in the control or prevention of illnesses, especially in the control of β-lactamase-forming pathogens alone or in combination with β-lactam antibiotics, i.e. antibiotics which contain a β-lactam ring, for example penicillins such as benzylpenicillin, phenoxymethylpenicillin, carbenicillin, methicillin, propicillin, ampicillin, amoxicillin and mecillinam, and cephalosporins such as cephaloridine, cephalotin, cefazolin, cephalexin, cefoxitin, cephacetrile, cephamandole, cephapirin, cephradine and cephaloglycin. The compounds of formula I or pharmaceutically acceptable salts thereof with bases can be administered before, simultaneously with or after the administration or intake of β-lactam antibiotics. If the compounds of formula I or pharmaceutically acceptable salts thereof with bases are administered simultaneously with a β-lactam antibiotic, then this can be carried out by administration as an ad-hoc combination or in the form of a pharmaceutical combination which contains a compound of formula I or a pharmaceutically acceptable salt thereof with a base and a β-lactam antibiotic; such pharmaceutical combinations are likewise an object of the present invention.

The dosage of the compounds of formula I and of the pharmaceutically acceptable salts thereof with bases can vary within wide limits and is, of course, adjusted in each particular case to the individual requirements and to the β-lactamase-producing pathogen to be controlled. In general, a daily dosage of about 0.1 to about 2.0 g should be appropriate. The daily dose can be administered in one or more unit dosages. The ratio of β-lactamase-inhibitor (compound of formula I or pharmaceutically acceptable salt thereof with a base) to β-lactam antibiotic can also vary within wide limits and is adjusted in each particular case to the individual requirements. In general, the weight ratio varies from about 1:20 to about 1:1 of compound I to the β-lactam antibiotic.

As mentioned earlier, medicaments containing a compound of general formula I or a pharmaceutically acceptable salt thereof with a base are also an object of the present invention, as is a process for the manufacture of such medicaments which comprises bringing a compound of formula I or a pharmaceutically acceptable salt thereof with a base and, if desired, one or more other therapeutically valuable substances into a galenical administration form; in this connection reference is again made to the pharmaceutical combinations mentioned above which are likewise an object of the present invention. In particular, pharmaceutical compositions containing a compound of formula I or a pharmaceutically acceptable salt thereof with a base and a β-lactam antibiotic, for example a penicillin such as benzylpenicillin, phenoxymethylpenicillin, carbenicillin, methicillin, propicillin, ampicillin, amoxicillin and mecillinam, or a cephalosporin such as cephaloridine, cephalotin, cefazolin, cephalexin, cefoxitin, cephacetrile, cephamandole, cephapirin, cephradine and cephaloglycin, are objects of the present invention. Such combinations are suitable for the control of β-lactamase-forming pathogens.

The following Examples illustrate the invention. Unless otherwise stated, percentages and ratios relating to solvent mixtures are expressed in volume, and the remaining percentages and ratios are expressed in weight. Temperatures are in degrees Celsius (°C.), normal pressure is about 1 atmosphere and room temperature is about 23° C. DBN is 1,5-diazabicyclo[4.3.0]non-5-ene. Unless indicated otherwise, the Examples were carried out as written.

EXAMPLE 1

A solution of 0.139 g (2 mmol) of hydroxylamine hydrochloride in 10 ml of ethanol is treated at 20° while stirring with 0.164 g (2 mmol) of sodium acetate and then there is added to this mixture a solution of 0.73 g (2 mmol) of methylene-(6Z)-6-acetonylidenepenicillanate pivalate in 30 ml of ethanol. After 1.5 hours, the mixture is evaporated, the residue is partitioned between ether and water, and the organic phase is separated and washed with water. The ether phase is dried over magnesium sulphate, filtered and evaporated. The residue is purified by filtration through silica gel using cyclohexane/ethyl acetate (7:3) for the elution. There is obtained methylene-(2S,5R)-6-[2-(hydroxyimino)propylidene]-pencillanate pivalate; IR (CHCl₃): 3580, 3350, 1770, 1604.

EXAMPLE 2

A solution of 0.835 g (10 mmol) of methoxyhydroxylamine hydrochloride in 100 ml of ethanol is treated at 20° while stirring with 0.82 g (10 mmol) of sodium acetate and to the suspension obtained there is added a solution of 3.7 g (10 mmol) of methylene-(6Z)-6-acetonylidenepenicillanate pivalate in 200 ml of ethanol. After 4 hours, the mixture is evaporated and the material obtained is purified by filtration through silica gel using cyclohexane/ethyl acetate (8:2) for the elution. There is obtained methylene-(2S,5R)-6-[(E/Z)-2-methoxyiminopropylidene]penicillanate pivalate; IR (CHCl₃): 1767, 1579, 1051.

EXAMPLE 3

0.435 ml (5 mmol) of morpholine is added dropwise to a solution, stirred at 20°, of 1.845 g (5 mmol) of methylene-(6Z)-acetonylidenepenicillanate pivalate in 40 ml of methylene chloride. After 22 hours, the mixture is evaporated and the residue is purified by filtration through silica gel using cyclohexane/ethyl acetate (6:4) for the elution. There is obtained methylene-(2S,5R,6S)-6-acetonyl-6-morpholino-penicillanate pivalate in the form of colourless crystals; IR (KBr): 2828, 1777, 1750, 1706, 1115.

EXAMPLE 4

1.84 g (5 mmol) of methylene-(6Z)-6-acetonylidenepenicillanate pivalate are dissolved in 30 ml of methylene chloride, treated at 20° with 0.51 ml (5 mmol) of thiophenol and a few drops of DBN, the mixture is stirred for 10 minutes and then evaporated under reduced pressure. The oil obtained is purified by filtration through silica gel using cyclohexane/ethyl acetate (8:2) for the elution. There is obtained methylene-(2S,5R,6S)-6-acetonyl-6-phenylthio-penicillanate pivalate in the form of an orange oil; IR: 1741, 1704.

EXAMPLE 5

A solution, stirred at 20°, of 1.845 g (5 mmol) of methylene-(6Z)-6-acetonylidenepenicillanate pivalate in 25 ml of methylene chloride is treated with 0.35 ml (5 mmol) of thioacetic acid and a few drops of DBN. After 6 hours, the crude product obtained after evaporation is purified by filtration through silica gel using cyclohexane/ethyl acetate (7:3) for the elution. There is obtained methylene-(2S,5R,6R)-6-acetonyl-6-acetylthio-penicillanate pivalate; IR (CHCl₃): 1781, 1770, 1720.

EXAMPLE 6

A suspension, stirred at 20°, of 1.65 g (10 mmol) of 2-hydrazinobenzothiazole in 75 ml of ethanol is treated dropwise with a solution of 3.7 g (10 mmol) of (6Z)-6-acetonylidenepenicillanate pivalate in a mixture of 100 ml of ethanol and 30 ml of tetrahydrofuran. After 1 hour, the suspension obtained is concentrated to 50 ml and filtered. The filtrate is evaporated under reduced pressure and the residue is purified by filtration through silica gel using cyclohexane/ethyl acetate (7:3) for the elution. There is obtained methylene-(2S,5R)-6-[[2-(2-benzothiazolyl)hydrazino]propylidene]penicillanate pivalate in the form of an orange coloured foam; IR: 3270, 1760, 1604, 1553, 1271.

EXAMPLE 7

A solution, stirred at 20°, of 0.6 g (5.7 mmol) of ethyl carbazate in 35 ml of ethanol is treated dropwise with 2.1 g (5.7 mmol) of methylene-(6Z)-acetonylidenepenicillanate pivalate in 50 ml of ethanol. After 48 hours, the mixture is evaporated and the residue is purified by filtration through silica gel using cyclohexane/ethyl acetate (6:4) for the elution. There is obtained methylene-(2S,5R,6S)-6-acetonyl-6-[(1-ethoxyformamido)amino]penicillanate pivalate; IR (KBr): 1763, 1716, 1263, 1112.

I claim:

1. A compound of the formula:

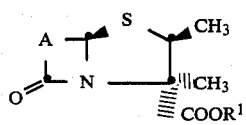

wherein $R^1$ is hydrogen or a group readily cleavable by hydrolysis: A is $R^2$—N=C(CH$_3$)—CH=C< or O=C(CH$_3$)—CH$_2$—(R$^3$)<; $R^2$ is hydroxy, lower alkoxy, 2-benzothiazoylamino or phenylamino; and $R^3$ is phenylthio, lower alkanoylthio, lower alkoxycarbonylhydrazino or morpholino, or a pharmaceutically acceptable salt thereof.

2. The compound of claim 1, wherein $R^1$ is hydrogen.

3. The compound of claim 1, wherein $R^1$ is alkanoyloxyalkyl, alkoxycarbonyloxyalkyl, lactonyl, alkoxymethyl or alkanoylaminomethyl.

4. The compound of claim 3, wherein $R^1$ is alkanoyloxyalkyl.

5. The compound of claim 4, wherein the alkanoyloxyalkyl is pivaloyloxymethyl.

6. The compound of claim 1, wherein $R^2$ is hydroxy.

7. The compound of claim 1, wherein $R^3$ is phenylthio.

8. The compound of claim 1, wherein $R^3$ is lower alkanoylthio.

9. The compound of claim 8, wherein the lower alkanoylthio is acetylthio.

10. The compound of claim 1, wherein $R^3$ is morpholino.

11. The compound of claim 1, wherein A is $R^2$—N=C(CH$_3$)—CH=C<.

12. The compound of claim 1, wherein A is O=C(CH$_3$)—CH$_2$—C(R$^3$)<.

13. The compound of claim 1, wherein $R^1$ is hydrogen or pivaloyloxymethyl; $R^2$ is hydroxy; and $R^3$ is phenylthio, acetylthio or morpholino.

14. The compound of claim 1, wherein the compound is methylene-(2S,5R)-6-[2-(hydroxyimino)propylidene]penicillanate pivalate.

15. The compound of claim 1, wherein the compound is methylene-(2S,5R,6S)-6-acetonyl-6-phenylthiopenicillanate pivalate.

16. The compound of claim 1, wherein the compound is methylene-(2S,5R,6R)-6-acetonyl-6-acetylthiopenicillanate pivalate.

17. The compound of claim 1, wherein the compound is methylene-(2S,5R,6S)-6-acetonyl-6-morpholinopenicillanate pivalate.

18. The compound of claim 1, wherein the compound is methylene-(2S,5R)-6-[[2-(2-benzothiazolyl)hydrazono]propylidene]penicillanate pivalate.

19. The compound of claim 1, wherein the compound is methylene-(2S,5R)-6-[1-(Z)-2-(methoxyimino)-propylidene]penicillanate pivalate.

20. The compound of claim 1, wherein the compound is methylene-(2S,5R,6S)-6-acetonyl-6-[1-(ethoxyformamido)amino]penicillate pivalate.

21. A beta-lactamase-inhibiting composition comprising (a) a compound of the formula:

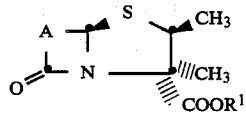

wherein $R^1$ is hydrogen or a group readily cleavable by hydrolysis: A is $R^2$—N=C(CH$_3$)—CH=C< or O=C(CH$_3$)—CH$_2$—(R$^3$)<; $R^2$ is hydroxy, lower alkoxy, 2-benzothiazolylamino or phenylamino; and $R^3$ is phenylthio, lower alkanoylthio, lower alkoxycarbonylhydrazino or morpholino, or a pharmaceutically acceptable salt thereof, in an amount which is effective for beta-lactamase inhibition; and (b) a pharmaceutically acceptabl carrier material.

22. The composition of claim 21, further comprising a beta-lactam antibiotic.

23. The composition of claim 21, wherein the weight ratio of compound I or a pharmaceutically acceptable salt thereof to the beta-lactam antibiotic is between about 1 to 20 and about 1 to 1.

24. The composition of claim 21, wherein the beta-lactam antibiotic is benzylpenicillin, phenoxymethylpenicillin, carbenicillin, methicillin, propicillin, ampicillin, amoxicillin, mecillinam, cephaloridine, cephalotin, cefazolin, cephalexin, cefoxitin, cephacetrile, cephamandole, cephapirin, cephradine or cephaloglycin.

25. A method for controlling beta-lactamase-forming pathogens in a mammal comprising administering to the mammal a compound of the formula:

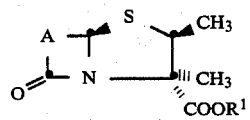

wherein $R^1$ is hydrogen or a group readily cleavable by hydrolysis: A is $R^2$—N=C(CH$_3$)—CH=C< or O=C(CH$_3$)—CH$_2$—(R$^3$)<; $R^2$ is hydroxy, lower alkoxy, 2-benzothiazoylamino or phenylamino; and $R^3$ is phenylthio, lower alkanoylthio, lower alkoxycarbonylhydrazino or morpholino, or a pharmaceutically acceptable salt thereof, in an amount which is effective for controlling beta-lactamase-forming pathogens.

26. The method of claim 25, wherein Compound I is administered in a daily dose of about 0.1 to about 2.0 g.

27. The method of claim 26, further comprising administering to the mammal a beta-lactam antibiotic.

* * * * *